(12) United States Patent
MacDonald et al.

(10) Patent No.: US 7,829,181 B2
(45) Date of Patent: Nov. 9, 2010

(54) SOLVATOCHROMIC VISUAL INDICATOR AND THE USE OF THE SAME

(75) Inventors: John Gavin MacDonald, Decatur, GA (US); Alison Salyer Bagwell, Cumming, GA (US); Yanbin Huang, Foster City, CA (US); Jaeho Kim, Roswell, GA (US); Stephanie Michelle Martin, Woodstock, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1308 days.

(21) Appl. No.: 11/216,731

(22) Filed: Aug. 31, 2005

(65) Prior Publication Data

US 2007/0048503 A1 Mar. 1, 2007

(51) Int. Cl.
*B32B 7/14* (2006.01)
(52) U.S. Cl. .................... 428/203; 428/913; 8/400; 283/96; 283/97
(58) Field of Classification Search ................ 428/203, 428/913; 8/400; 283/96, 97
See application file for complete search history.

(56) References Cited

U.S. PATENT DOCUMENTS

| | | | |
|---|---|---|---|
| 2,156,880 A | 5/1939 | Slomon |
| 3,414,415 A | 12/1968 | Broad, Jr. |
| 3,480,402 A | 11/1969 | Jackson |
| 3,520,124 A | 7/1970 | Myers |
| 4,229,813 A | 10/1980 | Lilly et al. |
| 4,292,916 A | 10/1981 | Bradley et al. |
| 4,643,122 A | 2/1987 | Seybold |
| 4,824,827 A | 4/1989 | Kelly et al. |
| 4,903,254 A | 2/1990 | Haas |
| 5,036,859 A | 8/1991 | Brown |
| 5,045,283 A | 9/1991 | Patel |
| 5,053,339 A | 10/1991 | Patel |
| 5,058,088 A | 10/1991 | Haas et al. |
| 5,107,470 A | 4/1992 | Pedicano et al. |
| 5,322,031 A | 6/1994 | Lerner et al. |
| 5,446,705 A | 8/1995 | Haas et al. |

(Continued)

FOREIGN PATENT DOCUMENTS

EP  0813850 A2  12/1997

(Continued)

OTHER PUBLICATIONS

Ellison, S, "Un-Pampered: Tots Face Strict Deadline on Toilet-Training," *The Wall Street Journal*, Aug. 27, 2004, 4 pages.

(Continued)

*Primary Examiner*—Betelhem Shewareged
(74) *Attorney, Agent, or Firm*—Richard M. Shane

(57) ABSTRACT

A graphic and/or message display system is described. The graphic and/or message display system functions to develop over a period of time a hidden graphic or message on an indicator panel or display area. The hidden graphic or message is revealed when an obscuring graphic reacts with a solvent to change color become at least substantially transparent. The graphic and/or message display system may be used as a stand-alone device or may be incorporated as part of various articles or products, for instance, as a positive reinforcement or a reminder to perform a task. Methods for using the graphic and/or message display system are also described.

14 Claims, 5 Drawing Sheets

U.S. PATENT DOCUMENTS

| | | | |
|---|---|---|---|
| 5,468,236 | A | 11/1995 | Everhart et al. |
| 5,469,145 | A | 11/1995 | Johnson |
| 5,518,927 | A | 5/1996 | Malchesky et al. |
| 5,602,804 | A | 2/1997 | Haas |
| 5,633,835 | A | 5/1997 | Haas et al. |
| 5,633,836 | A | 5/1997 | Langer et al. |
| 5,699,326 | A | 12/1997 | Haas et al. |
| 5,715,215 | A | 2/1998 | Haas et al. |
| 5,719,828 | A | 2/1998 | Haas et al. |
| 5,785,354 | A | 7/1998 | Haas |
| 5,796,345 | A | 8/1998 | Leventis et al. |
| 5,797,344 | A | 8/1998 | Ramsey et al. |
| 5,817,076 | A | 10/1998 | Fard |
| 5,822,280 | A | 10/1998 | Haas |
| 5,929,747 | A | 7/1999 | Rosenblatt et al. |
| 5,930,206 | A | 7/1999 | Haas et al. |
| 5,974,003 | A | 10/1999 | Pedicano et al. |
| 5,976,881 | A | 11/1999 | Klingner |
| 6,203,496 | B1 | 3/2001 | Gael et al. |
| 6,270,724 | B1 * | 8/2001 | Woodaman ............ 422/58 |
| 6,295,252 | B1 | 9/2001 | Holt et al. |
| 6,297,424 | B1 | 10/2001 | Olson et al. |
| 6,307,119 | B1 | 10/2001 | Cammarota et al. |
| 6,452,873 | B1 | 9/2002 | Holt et al. |
| 6,580,013 | B1 | 6/2003 | Belloso |
| 6,617,488 | B1 | 9/2003 | Springer et al. |
| 6,635,797 | B2 | 10/2003 | Olson et al. |
| 6,710,221 | B1 | 3/2004 | Pierce et al. |
| 6,752,430 | B2 | 6/2004 | Holt et al. |
| 6,790,670 | B2 | 9/2004 | Munagavalasa et al. |
| 6,796,065 | B2 | 9/2004 | Haas |
| 6,916,116 | B2 | 7/2005 | Diekmann et al. |
| 2003/0153891 | A1 | 8/2003 | Molee |
| 2004/0120904 | A1 | 6/2004 | Lye et al. |
| 2005/0124947 | A1 | 6/2005 | Fernfors |
| 2005/0130253 | A1 | 6/2005 | Lye et al. |
| 2005/0137542 | A1 | 6/2005 | Underhill et al. |
| 2005/0185520 | A1 | 8/2005 | Haas et al. |
| 2008/0057534 | A1 * | 3/2008 | Martin et al. ............ 435/34 |

FOREIGN PATENT DOCUMENTS

| | | |
|---|---|---|
| JP | 2000-292563 | 10/2000 |
| JP | 2002153503 | 5/2002 |
| WO | WO 01/82004 | 11/2001 |
| WO | WO 01/86289 | 11/2001 |
| WO | WO 01/87132 | 11/2001 |
| WO | WO 02/075441 | 9/2002 |
| WO | WO 03/007088 | 1/2003 |
| WO | WO 03/070138 | 8/2003 |
| WO | WO 2005/039656 | 5/2005 |
| WO | WO 2005/048902 | 6/2005 |
| WO | WO 2005/058114 | 6/2005 |
| WO | WO 2005/058119 | 6/2005 |
| WO | WO 2005/059162 | 6/2005 |
| WO | WO 2006/060060 | 6/2006 |

OTHER PUBLICATIONS

Pepe, R. C. et al., "Colorant Cross Index," *International Cosmetic Ingredient Dictionary and Handbook*, 9th Ed., vol. 4, Sect. 12, 2002, published by The Cosmetic, Toiletry, and Fragrance Association, ISBN: 1-882621-29-8 (4- volume set), pp. 3195-3199.

Spock, B., M.D., and Rothenberg, M.B., M.D., "Toileting-What Does It Mean?", *Dr. Spock's Baby and Child Care*, 6th Ed., 1992, ISBN: 0-671-75967-1, pp. 457-475.

"Fatty Acids", http://www.cyberlipid.org/fa/acid0001.htm, viewed and printed Feb. 3, 2005, pp. 1-15.

* cited by examiner

SOLVATOCHROMIC VISUAL INDICATOR AND THE USE OF THE SAME

BACKGROUND

Many products, for example, personal care products, are intended to be used for a particular, limited, period of time. In some circumstances it would be advantageous for the product to visually convey a message to the individual using the product at a particular time during the use of the product. For example, a small child using a training pant could be positively reinforced after wearing the training pant for some extended period of time. As another example, many disposable products should be replaced after a defined period of time. After the designated time, the products may have lost some efficacy, thus making it advantageous for the wearer of the product to replace the old product with a new product. A graphic or message appearing on the product at the designated time would alert the wearer and those in the immediate surroundings that it is time to change the product.

Therefore, a need exists for a graphic and/or message display system for causing a graphic or message to appear on a product at a designated time and a method for using the system. The message should be easy to see. Additionally, the system should be easy to activate at the start of the use of the product. Desirably, the system can be tailored to cause the message to appear at a particular time depending on the particular product. The present invention addresses the aforementioned need.

SUMMARY OF THE INVENTION

The systems, devices, and methods described herein can be adapted to a host of potential products and uses for which there may be a need for conveying a graphic or message on a display area at a particular time.

In general, a device or system includes an indicator panel or display area on a first substrate that includes a hidden graphic or message that will be revealed at a prescribed time. As used herein, the term "indicator panel" or "indicator display" refers to any surface, shape or geometric configuration upon which a message may be displayed or manifested at a particular time during use of the device. The display area may encompass a variety of surfaces or shapes. For instance, the basic indicator panel may be a flat, essentially two-dimensional surface. Alternatively, the indicator panel may have a three-dimensional curved surface, or be part of a shaped article or geometric form. On the indicator panel is situated an obscuring graphic that obscures or hides the hidden graphic or message until the prescribed time for revealing the hidden graphic or message. The obscuring graphic desirably includes a solvatochromic dye. More desirably the obscuring graphic includes a betaine or a zwitterionic dye, and even more desirably includes Reichardt's dye.

The system further includes a second substrate or solvent applicator coated with a solvent. During use of the system, the second substrate is positioned such that the solvent is placed in controlled communication with the obscuring graphic overlying the hidden graphic or message. The second substrate is desirably substantially transparent so as to not obscure the underlying graphics. Even more desirably, the second substrate may be a clear sheet-like material, film, tape, and so forth. The solvent, once placed in controlled communication with the obscuring graphic, interacts with the obscuring graphic to cause at least portion of the graphic to become substantially transparent, disappear, or change color, thus causing the appearance of the hidden graphic or message.

The indicator panel can take the form of either a substantially two-dimensional visual presentation or be part of a three-dimensional shaped surface or article. The display area of the message can be of a size that ranges from an object that one is capable of holding within an average person's hand (e.g., linearly on the scale of about 2 or 3-12 inches or larger (about 4 or 5 cm to $\leqq$20-30.5 cm)) to an object as large as a billboard (i.e., on the scale of one or two meters to several meters). The active portion of the indicator panel can be composed of any materials upon which the hidden and obscuring graphics can be affixed, for example, cellulose or cellulose-polymer-based materials, metal surfaces, plastic/polymer surfaces, plastic/polymer films, nonwoven materials, woven materials, and so forth. The solvent may include either a liquid, a gel, or semi-solid material. The solvent may be, for example, water, a thixotropic material, an alcohol, a non-flammable solvent, an adhesive material, other organic species, and so forth.

After application of the second substrate coated with the solvent to the indicator panel, the solvent is located between the second substrate and the indicator panel. When the solvent contacts the obscuring graphic, establishing communication between the solvent and the obscuring graphic, the obscuring graphic becomes activated. Once activated, the solvent enters or reacts with the obscuring graphic, causing a portion of the obscuring graphic to disappear or change color to reveal the hidden graphic or message. The rate at which the solvent reacts with the obscuring graphic may be expressed, for instance, on the order of minutes, hours, or days. Thus, the system can be designed to display the hidden graphic or message at a wide range of times, depending upon the particular need.

In another aspect, a method for providing a positive feedback to reinforce and condition an activity is described. The method includes providing a hidden graphic or message on an indicator panel, obscuring the hidden graphic or message with an obscuring graphic, activating the obscuring graphic with a solvent, which causes at least a portion of the obscuring graphic to disappear or change color, and revealing a hidden message or graphic when the obscuring graphic disappears or changes color.

An application for the basic system or device can be as a training aid for conveying a positive feedback to reinforce maintenance of dryness in a child's training pant. The indicator panel on the training aid has a hidden message which manifests itself on the indicator panel after a predetermined period of time for which it is desired that the training pant be worn, through the development of the hidden graphic or message over the course of the predetermined time period, hence providing a positive feedback signal. The predetermined period of time can be controlled by selection of different solvents to apply to the obscuring graphic. Therefore, a parent can start a child with a short period of time at which the positive feedback will be revealed. As the child becomes more trained, the use of a different solvent can extend the period of time required to reveal the positive feedback. The revelation of the hidden graphic or message, according to an embodiment, can appeal to children and enhance their willingness to use the training aid.

The invention also describes the use or incorporation of at least one indicator device for displaying hidden graphics or messages after a particular period of time with any suitable personal care products, medical or surgical articles or garments. As used herein, the term "personal care product" refers to articles such as diapers, training pants, absorbent underpants, and adult incontinence products. Also, as used herein, the term "medical or surgical article or garment" refers to medically or therapeutically oriented items such as surgical gowns and drapes, face masks, head coverings like bouffant caps, surgical caps and hoods, examination and surgical gloves, footwear like shoe coverings, boot covers and slippers, wound dressings, bandages, sterilization wraps, wipers, garments like lab coats, coveralls, aprons and jackets, patient bedding, stretcher and bassinet sheets, and the like. Alternatively, the present indicator device for displaying hidden graphics or messages after a particular time can be used in conjunction with medical devices, such as disposable catheters, tubes, tracheal tubes, and the like, which may require periodic maintenance.

The device includes a display having a hidden message or graphic obscured by an obscuring graphic, and having a substrate coated with a solvent that, when the solvent is brought into communication with the obscuring graphic, will interact with the obscuring graphic and cause a portion of the obscuring graphic to disappear or change color over a predetermined time period, thus causing the originally obscured message or graphic to appear. In certain embodiments, the article or absorbent garment can include at least an absorbent core and an outer sheet around the core. Furthermore, the absorbent garment may have a top sheet; a back sheet; and absorbent core disposed at least partially between the top sheet and back sheet.

In another embodiment, a method for providing improved hygiene habits includes providing an indicator panel having a graphic region including a solvatochromic dye; providing a solvent applicator including a transparent sheet-like substrate having first and second surfaces, and a solvent disposed on the first surface of the substrate; and, placing the solvent in controlled communication with the solvatochromic dye to convey a message.

Additional features and advantages of the graphic and/or message display system and associated articles of manufacture and methods will be disclosed in the following detailed description. It is understood that both the foregoing summary and the following detailed description and examples are merely representative of the invention, and are intended to provide an overview for understanding the invention as claimed.

BRIEF DESCRIPTION OF FIGURES

A full and enabling disclosure of the present invention, including the best mode thereof to one of ordinary skill in the art, is set forth more particularly in the remainder of the specification, including reference to the accompanying figures in which.

Figure 1:
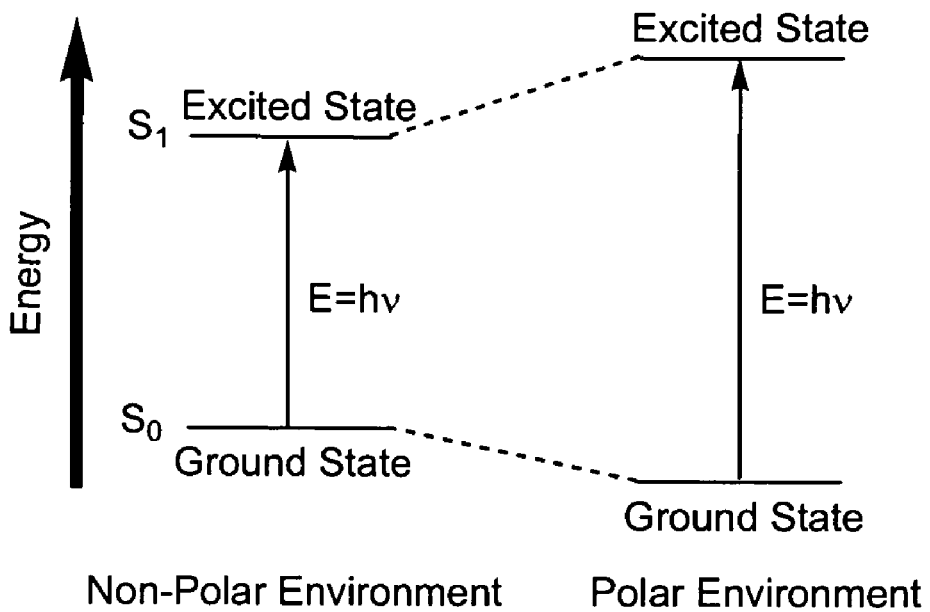
FIG. 1 depicts a schematic representation that illustrates the energy states of merocine.

Repeat use of reference characters in the present specification and drawings is intended to represent the same or analogous features or elements of the invention.

DETAILED DESCRIPTION OF THE INVENTION

Reference will now be made in detail to various embodiments of the invention, one or more examples of which are set forth below. Each embodiment is provided by way of explanation of the invention, not limitation of the invention. In fact, it will be apparent to those skilled in the art that various modifications and variations may be made in the present invention without departing from the scope or spirit of the invention. For instance, features illustrated or described as part of one embodiment, may be used on another embodiment to yield a still further embodiment. All technical and scientific terms used herein have the usual meaning conventionally understood by persons skilled in the art to which this invention pertains, unless context defines otherwise. The present invention is not necessarily limited to specific compositions, materials, designs or equipment, as such may vary. As used in this specification and the appended claims, the singular forms "a," "an," and "the" include plural referents unless the context clearly dictates otherwise. Thus, it is intended that the present invention cover such modifications and variations as come within the scope of the appended claims and their equivalents.

As used herein, and in the claims, the term "comprising" is inclusive or open-ended and does not exclude additional unrecited elements, compositional components, or method steps. Accordingly, such term is intended to be synonymous with the words "has", "have", "having", "includes", "including", and any derivatives of these words.

In one embodiment, a graphic and/or message display system has an indicator panel or display area upon which an initially obscured graphic or message can be rapidly and easily observed or determined after the passage of a predetermined period of time. Desirably, the graphic and/or message display system is displayed on a product that includes at least one major surface that forms an active display area of the indicator panel. The transformation of the obscured or hidden graphic or message can be activated by the user at some time $T_0$ and the hidden graphic or message appears after a predetermined time period $T_x$, hence providing some notification to a user of the product. It is envisioned that the device will be used for a variety of applications in which the conveyance of a graphic or message after a predetermined period of time would be advantageous. In other embodiments, the invention includes associated articles of manufacture and methods for using the graphic and/or message display system to display hidden graphics and/or messages.

In one aspect, an obscuring graphic is used to obscure the hidden graphic or message until the time at which the hidden graphic or message is revealed. Desirably, a solvatochromic dye is used to obscure the hidden message or graphic. Solvatochromic dyes are a unique class of dyes that become transparent, become substantially transparent, or undergo a color change when the molecular environment, such as solvent polarity, hydrogen bonding propensity, and so forth, changes. Thus, the same dye has different colors and/or transparency when dissolved in different solvents.

In another aspect, a non-solvatochromic dye having a first color may be mixed with a masking solvatochromic dye to create a dye mixture having a second color. The dye mixture is used to create an initial graphic on the surface of an indicator panel. After application of a solvent to the dye mixture, the color of the graphic changes as the solvatochromic dye changes color (to create a third color) or becomes transparent (to reveal the first color).

In a further aspect, a solvatochromic dye is used to initially create a message or graphic on the indicator panel that will fade or disappear with time after exposure to a solvent. The initial message or graphic or design is obtained by applying the solvatochromic dye to a surface of the indicator panel, either directly or via a solution. After application of a solvent to the solvatochromic image, the image fades over time and eventually disappears, thus alerting or informing the user that a specific period of time has passed.

The color change of solvatochromic dyes may be attributed to differences in molecular or electron charge distributions in the ground and first allowed excited state of the solvatochromic dyes. In most dyes, electron density changes are comparatively small between the ground and first excited state. Because of this, the polarity of the solvent surrounding the dye molecule has only a small effect on the energy levels of the ground and excited states, giving rise to only a small net change in transition energy between the two states. In the case of certain dye structures, however, large changes between the ground and first excited state give rise to significant effects caused by polarity changes. Hence, in solvatochromic dyes, the interaction of the surrounding solvent with the ground and excited states of the dye depends on the polarity of the solvent. The energy levels of the ground and excited states may be shifted either closer together or further apart in energy, depending upon the type of dye involved and the environment or solvent in which it is found. For example, if the ground state of the dye is very polar, the ground state of the dye will be stabilized, or reduced in energy, when in a polar environment. Similarly, if the excited state of the dye is polar, the excited state will be stabilized in polar solvents and destabilized (or increased in energy) when the dye is in non-polar environments.

The difference between the polarity of the ground and excited states of many dyes is small, and so the net change in transition energy in differing environments is also small. Solvatochromic dyes are unusual in that the polarity of the lowest energy allowed excited state is very different from that of the ground state. In other words, significant changes in atomic electron densities are associated with electronic transitions which lead to large changes in the transition energy for the molecule in different environments.

This phenomenon may be depicted using a state diagram, such as the state diagram depicted in FIG. 1. FIG. 1 shows a state diagram for a dye with a ground state ($S_0$) that is more polar than the excited state ($S_1$). When transitioned from a non-polar environment to a polar environment, the ground state is stabilized (reduced energy), and the excited state is destabilized (increased energy), thus increasing the transition energy (E), thereby causing a hypochromic shift (a shift of the maximum absorption wavelength to shorter wavelengths, or a "red shift" in color).

An example of a dye that has a ground state more polar than the excited state is the merocyanine dye, depicted directly below in both the ground state and the excited state. The molecule on the left (1) is a major contributor to the ground state of the dye whereas the molecule on the right (1') is a major contributor to the first excited state of the dye.

Figure 2:
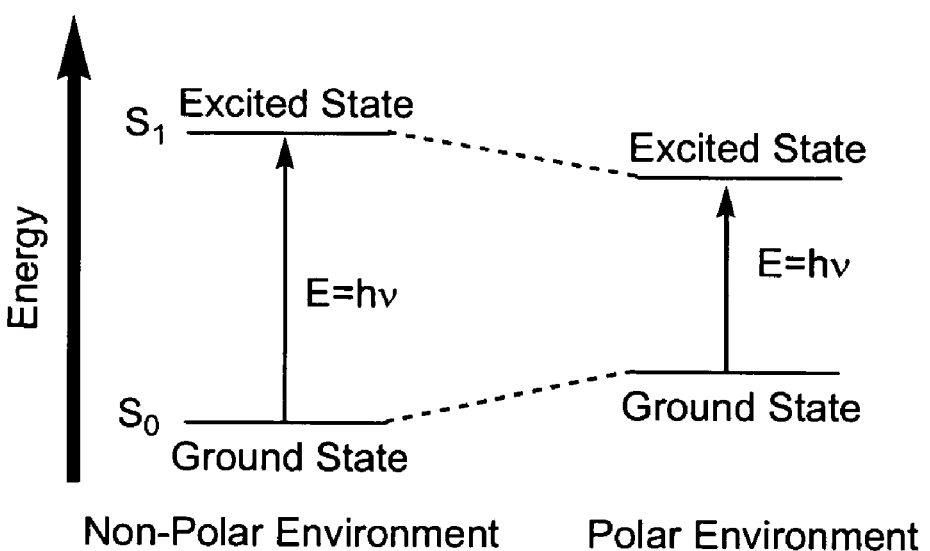
FIG. 2 depicts a schematic representation that illustrates the energy states of indigo.
Figure 3A:
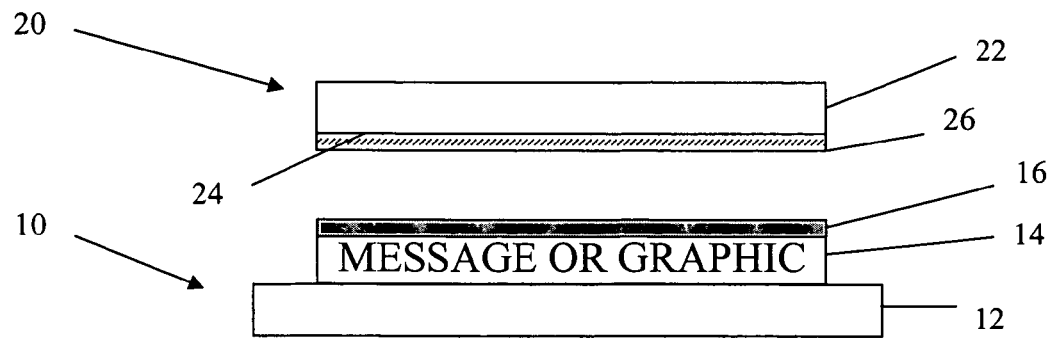
FIGS. 3a-c depict a schematic representation of a graphic and/or message display system and use thereof.
Figure 3B:
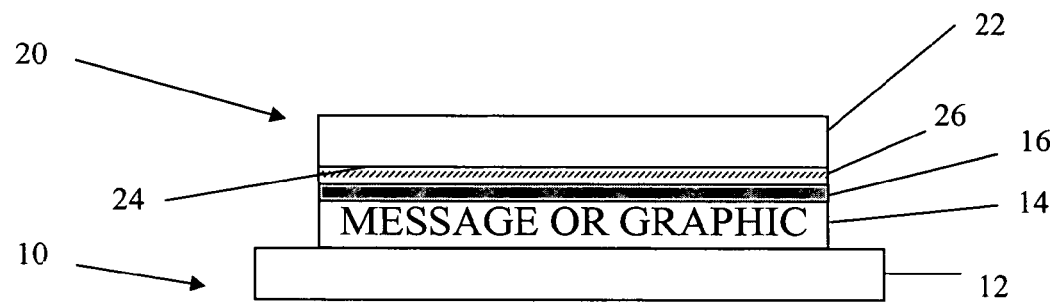
Figure 3C:
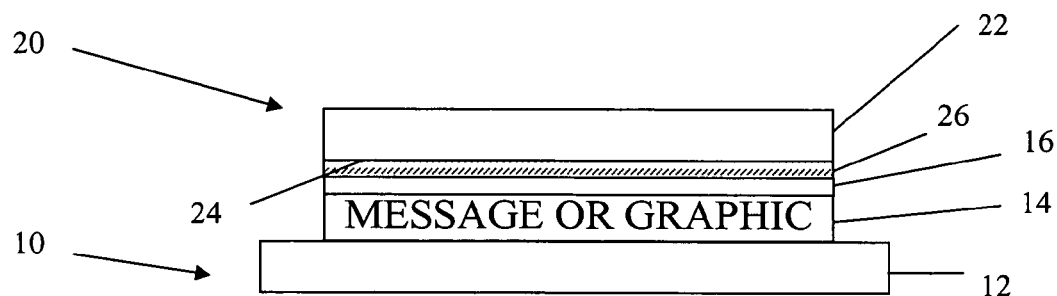

FIG. 2 shows a state diagram for a dye with a ground state ($S_0$) that is significantly less polar than the excited state ($S_1$). When transitioned from a non-polar environment to a polar environment, the ground state is destabilized (increased energy), and the excited state is stabilized (decreased energy), thus decreasing the transition energy (E), thereby causing a bathochromic shift (a shift of the maximum absorption wavelength to longer wavelengths, or a "blue shift" in color).

An example of a dye that has a ground state significantly less polar than the excited state is the indigo dye, depicted directly below in both the ground state and the excited state. The molecule on the left (2) is a major contributor to the ground state of the dye, whereas the molecule on the right (2') is a major contributor to the excited state of the dye.

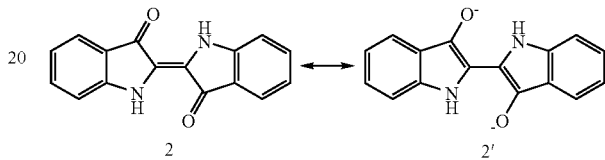

Thus the color and/or transparency of solvatochromic dyes depends upon the immediate environment of the dye. Solvent polarity, as well as hydrogen bonding and other environmental factors, plays a significant role in determining the state energy levels that in turn determine the color and/or transparency of the dye.

Suitable dyes for the practice of this invention include those discussed above as well as Reichardt's dye, merocyanine dyes, zwitterionic dyes, 4-[2-N-substituted-1,4-hydropyridin-4-ylidine)ethylidene]cyclohexa-2,5-dien-1-one, red pyrazolone dyes, azomethine dyes, indoaniline dyes, diazamerocyanine dyes, and mixtures thereof. Zwitterionic dyes (or chromogens) are dyes in which formal positive and negative charges are contained within a contiguous π-electron system.

Merocyanine dyes fall within a donor-simple acceptor chromogen classification as described by Griffiths in "Colour and Constitution of Organic Molecules" Academic Press (London) 1976, wherein a carbonyl group acts as an electron acceptor moiety. The electron acceptor is conjugated to an electron donating group, for instance, a hydroxyl or an amino group that is able to donate electrons. Merocyanine dyes are a relatively broad class of dyes that includes structure 3 directly below, wherein a nitrogen atom contained in a heterocyclic system serves as a donor. "n" may take any integer value including 0. Merocyanine dyes may have a charge separated (zwitterionic) resonance form as shown by structure 3'.

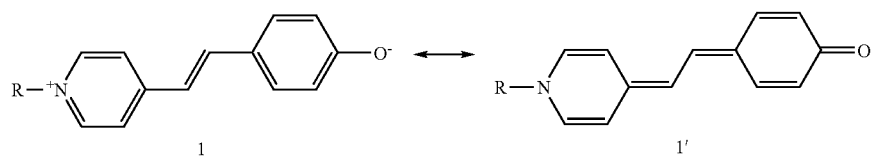

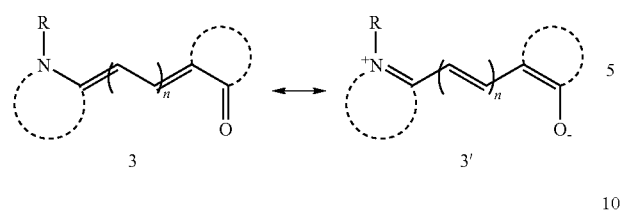

3     3'

Acyclic merocyanine dyes are also known, including vinylalogous amides.

Merocyanine dyes have been studied for their ability to photosensitize silver halide to certain wavelengths of light for use in photographic film. Many merocyanine dye structures are know. Structures or chemical formulas 4-14 shown directly below include several non-limiting examples of merocyanine dyes. It is noted that for each of these dyes, a charge separated resonance structure that may contribute significantly to the ground state of the dye may be drawn. Various substituents groups may be substituted for R, including methyl, alkyl, aryl, and phenyl groups, and so forth.

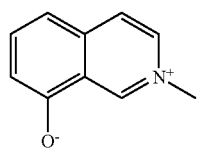
4

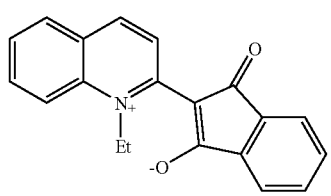
5

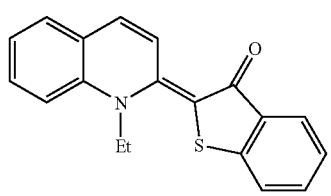
6

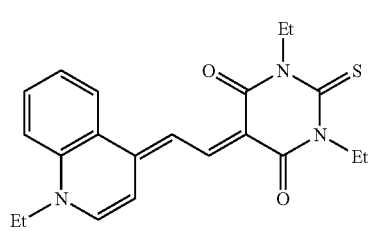
7

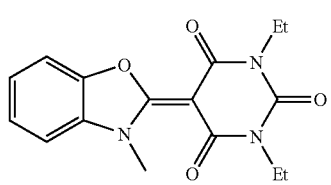
8

-continued

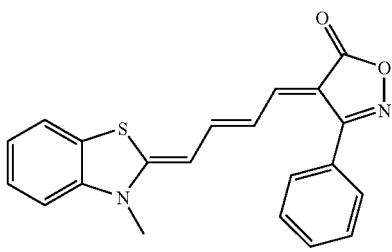
9

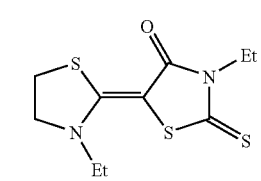
10

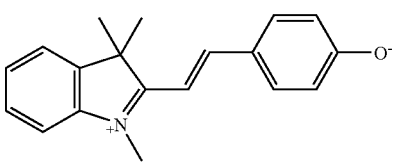
11

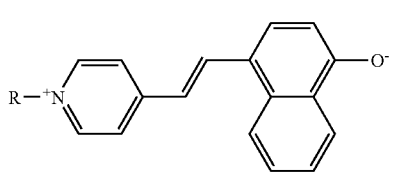
12

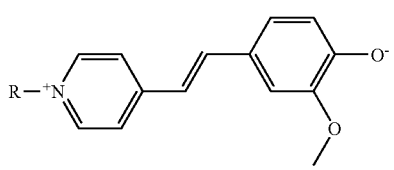
13

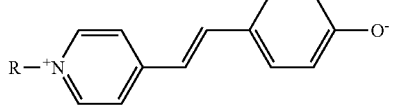
14

Zwitterionic dyes or chromogens may be prepared that are permanently of a zwitterionic form. That is to say, these dyes have permanent charges associated with the π-electron system and a neutral resonance structure for the chromogen cannot be drawn. Such dyes include Reichardt's dye, structure 15 below, which conforms to the general chemical formula 16 shown below.

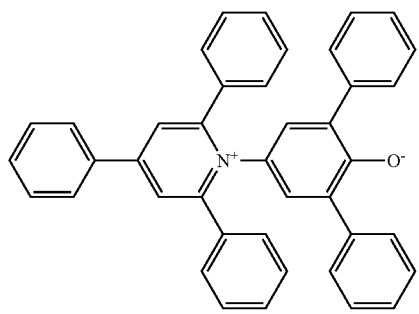
15
The chemical formulas of other examples of suitable solvatochromic pyridinium N-phenolate betaine dyes are set forth below as structures 16-21:
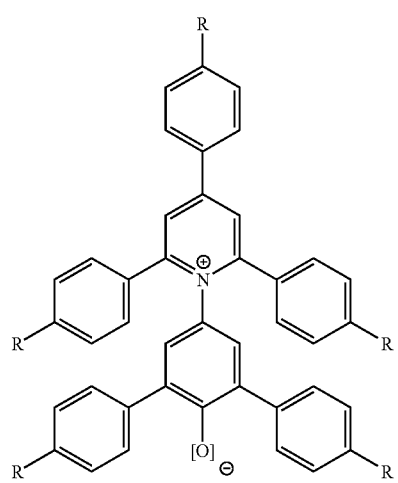
16
where R may be, for example, hydrogen,
—C(CH₃)₃, —CF₃, or C₆F₁₃.
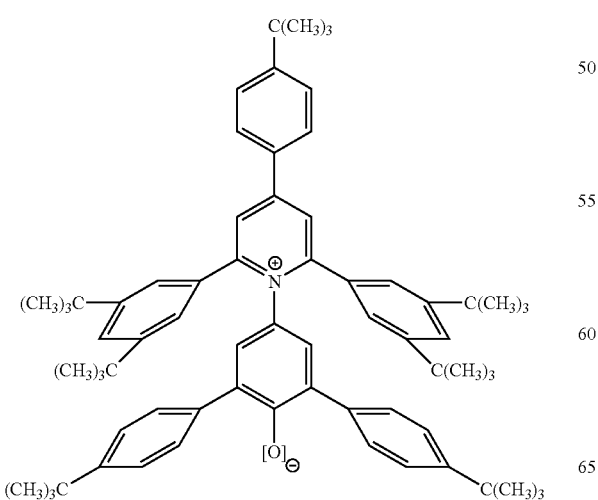
17
-continued
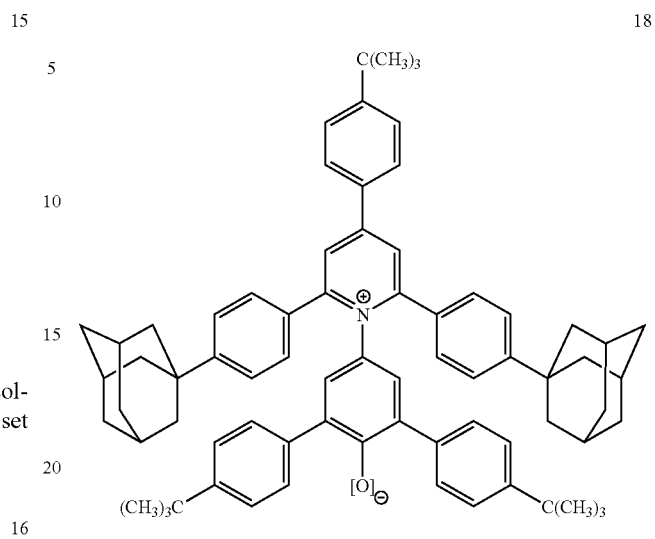
18
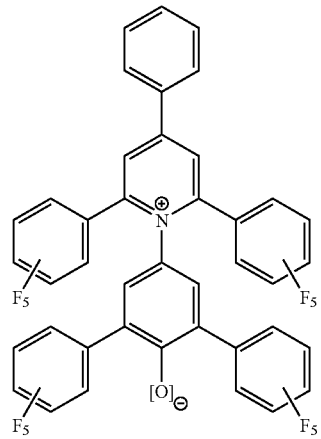
19
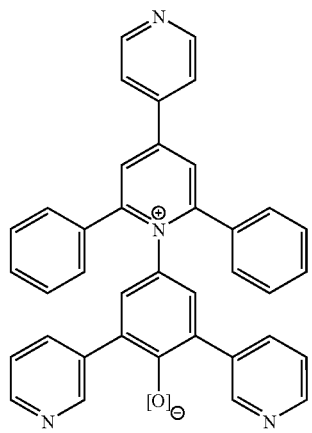
20

-continued

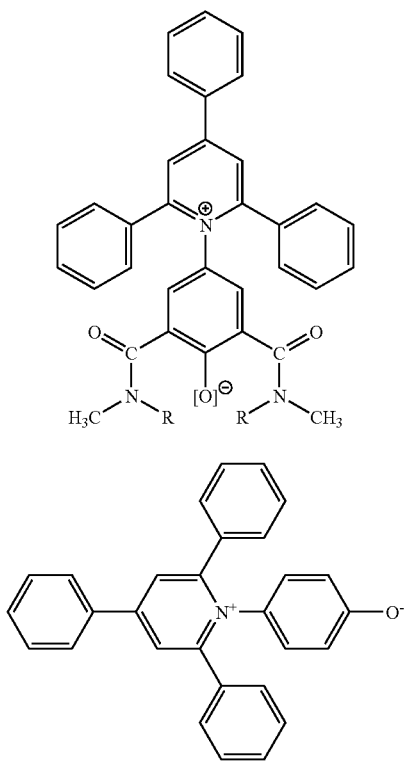

21

22

Additional solvatochromic dyes conforming to the general chemical formula 23 are shown as chemical formulas 24-32:

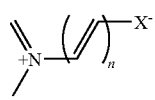

23 where X may be, for example, oxygen, carbon, nitrogen, or sulfur.

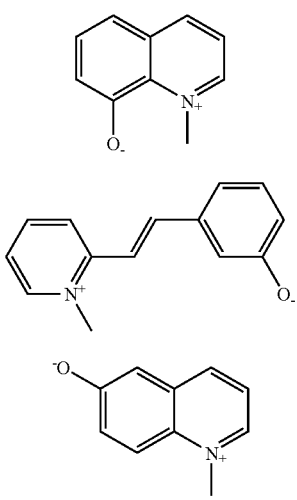

24

25

26

-continued

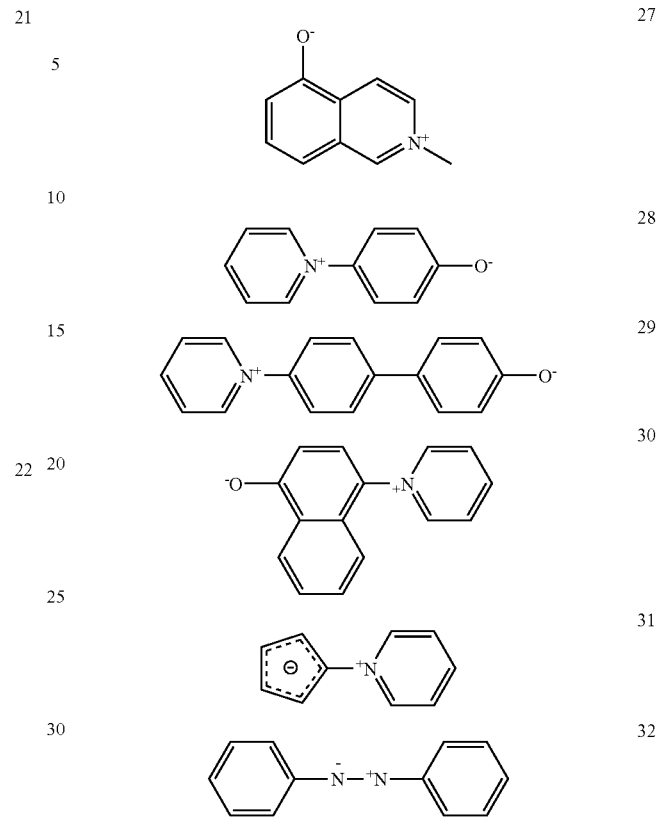

27

28

29

30

31

32

Other examples of solvatochromatic dyes may include, for instance: Reichardt's dye (available from Aldrich Chemical Co., Milwaukee, Wis.), 1-Docosyl-4-(4-hydroxystyryl)-pyridinium bromide (Aldrich Chem Co. Inc., Milwaukee Wis.), 2,6-dichloro-4-(2,4,6-triphenyl-N-pyridinio)-phenolate (hereinafter described as Betaine 1), 1-(4-hydroxyphenol)-2,4,6-triphenylpyridinium hydroxide (hereinafter described as Betaine 2), other pyridinium N-phenoxide betaines, and so forth. Reichardt's dye is a phenolbetaine, which shows very strong solvatochromism, the chemical structure of which is shown directly below ($R_1$-$R_5$=phenyl):

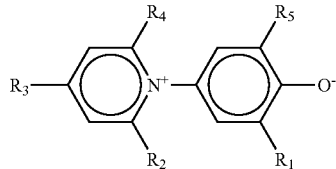

Even other solvatochromic dyes may be obtained by substitution of various groups for $R_1$-$R_5$ in the betaine phenolate structure shown above. The $R_1$, $R_2$, $R_3$, $R_4$, and $R_5$ groups may be, for example, phenyl, benzyl, pyridinyl, aryl, heteroaryl, alkyl ($C_1$-$C_{12}$), cycloalkyl, heterocyclo, halide, including chlorine, fluorine, and so forth, hydrogen, amido, amine, and thiol groups, and so forth.

The colors of Reichardt's dye dissolved in different solvents are shown in Table 1.

TABLE 1

Colors of Reichardt's dye in various solvents

| | |
|---|---|
| glycerin - | orange/pink |
| tetrahydrofuran - | dark green |
| pyridine - | turquoise |
| dimethylformamide - | light green |
| isopropanol - | light blue |
| acetonitrile - | light purple |

The colors of additional solvatochromic dyes dissolved in different solvents are shown in Table 2.

TABLE 2

Colors of solvatochromic dyes in various solvents

| Solvatochromic Dye | Solvent 1 Acetonitrile | Solvent 2 Acetone | Solvent 3 isopropanol |
|---|---|---|---|
| Betaine RD ($R1$—$R5$ = phenyl) | Magenta | Yellow | light blue |
| Betaine 1 dichloro ($R1$, $R5$ = Cl, $R2$—$R4$ = phenyl) | purple | Violet | magenta |
| Betaine 2 ($R1$, $R5$ = H, $R2$—$R4$ = phenyl) | Blue | Green | violet |

Solvatochromic dyes of this class have been synthesized, covalently immobilized onto a silica or polystyrene solid support or substrate, and changes in color in response to different solvents can be measured. Immobilization on the substrate can be achieved through a link from the 4 position of R3 to the solid support, and the spectral response of the dye can be modified by varying the substituents $R_1$, $R_2$, $R_3$, $R_4$, and $R_5$.

Generally, as depicted in the accompanying FIGS. 3-6, a product 10 has an indicator panel or display area 12 for displaying a hidden graphic or message 14. As shown in FIG. 3a, the hidden graphic or message 14 is obscured by an obscuring graphic 16. A solvent applicator 20 includes a solvent substrate 22 that has a coated surface 24 upon which is a solvent 26. Before use, the solvent 26 is coated or otherwise stored on the coated surface 24 of the solvent substrate 22. As depicted in FIG. 3b, the solvent 26 can be applied to the obscuring graphic 16 by placing the coated surface 24 of the solvent substrate 22 in contact with the obscuring graphic 16 on the indicator panel 12. As depicted in FIG. 3c, over a period of time, the solvent 26 interacts with the obscuring graphic 16 to cause the hidden graphic or message to become visible.

The indicator display area 12 may appear in any convenient shape, for example, in the general configuration of a strip, belt, or other linear conformation, in which one dimension is significantly greater or longer than another. According to one design, the indicator display area 12 may be incorporated as part of a belt that wraps around a user's wrist or waist, or as part of suspenders or other article clipped to a garment. In another embodiment, the indicator display 12 may be in the form of a patch or other conformation having a wide and large surface area. The indicator display 12 may have a particular design, motif, or shape (e.g., circle, square, rectangle, triangle, polygon, sunburst, star, stripes, flower, animal, vegetable, or article (toy-shape or silhouette, hammer, wand, gun, sword, etc.)). When in the form of a patch, the indicator display area 12 may be incorporated as part of the outer surface of a variety of products and articles, such as a garment, safety device, or absorbent article (e.g., diaper, inflatable float, pad). The indicator display 12 may be any substrate to which a hidden graphic may be imparted and obscured by a solvatochromic dye. The substrate to which the graphic is applied may include, but is not limited to, paper, wood, a wood product or composite, woven fabrics, non-woven fabrics, textiles, films, plastics, and the like. In one aspect, the graphic may be applied to textile articles, such as cloth.

Any solvent 26 or surface that causes the transformation of the color of the dye over time may be used to display an underlying message or graphic. For example, solvents that may be effective include water, aqueous detergent solutions, acidic water solutions, alkaline water solutions, isopropanol, ethanol, methyl-ethyl ketone, acetone, toluene, hexane, ethyl acetate, acetic acid (vinegar), cetyl alcohol (fatty alcohol), dimethicone silicone, isopropyl lanolate, myristate, palmitate, lanolin, lanolin alcohols and oils, octyl dodecanol, oleic acid (olive oil), panthenol (vitamin B-complex derivative), stearic acid and stearyl alcohol, butylene glycol and propylene glycol, cyclomethicone (volatile silicone), glycerin, aloe, petrolatum, and so forth. Viscous solvents, such as for example, common tape adhesives, have been found to be particularly effective at delaying or controlling the onset of the color change. Adhesives that may be useful include, for example, those based on alkyds, animal glues, casein glues, cellulose acetates, cellulose acetate butyrates, cellulose nitrates, ethyl celluloses, methyl celluloses, carboxy methyl celluloses, epoxy resins, furane resins, melamine resins, phenolic resins, unsaturated polyesters, polyethylacrylates, polymethylmethacrylates, polystyrenes, polyvinylacetates, polyvinylalcohols, polyvinyl acetyls, polyvinyl chlorides, polyvinyl acetate chlorides, polyvinylidene copolymers, silicones, starched based vegetable glues, urethanes, acrylonitrile rubbers, polybutene rubbers, chlorinated rubbers, styrene rubbers, and so forth. Skin contact adhesives and acrylic polymer-based DURO-TAK adhesives (available from National Starch & Chemical Company of Berkeley, Calif.) have also been shown to be useful. Waxes such as, for example, polyolefin waxes, bees waxes, and so forth, and gels such as, for example, glycol dimethacrylate, chitosan, polyacrylates, hydroxypropylcellulose, gelatin, and so forth, may also be useful to effect the color change. Without wishing to be bound by a particular theory, it is believed that a viscous solvent delays penetration of the dye into the solvent, thereby delaying the color change. The time duration to turn colorless can also be controlled by varying the concentration of the solvatochromic dye used and the thickness of the resulting coating. Application of more dye will result in a longer period of time to de-colorize. The period of time for de colorization may be varied from about 1 to about 5 hours.

The solvent 26 may be applied to the hidden graphic or message by any convenient method. For example, the solvent may be applied by pouring, brushing, wiping, and so forth. In one desirable embodiment, the solvent may be applied or coated on a substrate that is then placed such that the solvent is in communication with the hidden graphic or message. Substrates that may include, for example, films, fabrics, including woven and nonwoven fabrics, paper, laminates thereof, and so forth. Desirably, the substrate will be at least substantially transparent so that it can remain in place to hold the solvent in communication with the graphic and still allow the graphic to be visible through the substrate. A particularly advantageous substrate is a clear transparent polymer film. Suitable material examples for making such films may include polyolefins (e.g. polypropylene, polyethylene, and so forth), polyesters (e.g., PET), polyamides (e.g., nylon), silicones, and so forth.

Broader applications of this novel technology to health care garments and articles, diapers, product shelf-life indicators, stand alone timers for children are possible. In addition, hidden graphics or other messages could be placed on LITTLE SWIMMERS® disposable swimsuits to indicate when to apply more sun-screen to the child.

The graphic and/or message display system can be tailored to develop over any predetermined time frame and for any type of application in which one would need to display a graphic or message at a predetermined time. The graphic and/or message display system can be used in a number of formats and adapted for various applications, for example, clinical/medical uses, food and beverage related monitoring, hygiene training, and so forth. The graphic and/or message display system may be included in an assembly or kit with or attached to other items that may have time-dependent or time-influenced functionality or use.

The graphic and/or message display system can be a disposable, self-contained tool, which can be used in virtually any environment where it is desired that a message be displayed after a specified duration. The graphic and/or message display system also can be used as a training aid or tool to reinforce or condition one to perform certain activities. For instance, with young children who are potty-training, the delayed appearance of a positive message can help motivate them to stay dry over an ever longer duration. The graphic and/or message display system can be adjusted or tuned to develop in a prescribed amount of time, depending on the particular purpose.

The following descriptions serve as illustrative examples of several fields in which the graphic and/or message display system may be employed. The graphic and/or message display system could be deployed as a stand-alone device or be part of a package assembly or kit with other articles or components to help in medical or clinical settings as a general reminder system for patient care, which can unburden the caregiver and put control in the hands of patients. For example, a reminder message at a predetermined period of time could help patients monitor for how long medication is effective or be cognizant of the time a dosage of a drug should be taken (e.g., 4-hour dosage times at which time a message appears, avoiding over medication), serve as notification that a treatment (e.g., bone cement, plaster, dental adhesive, whitening treatment or skin treatments, etc.) is complete, serve as a reminder for wound dressing changes or draining, and so forth.

Furthermore, one can employ the graphic and/or message display system in food-related areas, such as a freshness indicator for the length of time something (e.g., coffee, baked goods, deli goods, vegetables/produce, buffet or fast food, airline food, or other products) has been stored or sitting. Beverage-related uses may include individual alcohol drink reminders (i.e., 1 drink/hour is recommended)—the drinker applies the solvent to the graphic when he or she begins drinking and when the message is displayed it would be acceptable to have another drink. The graphic and/or message display system could be used as a "flatness" indicator for carbonated beverages (soda, beer, etc.)—apply the solvent when the beverage container is first opened and when the message appears the drink has gone flat. Furthermore, the graphic and/or message display system could be used as a reminder for when a red wine has been allowed sufficient time to breath.

Similarly, the graphic and/or message display system can also be used for or packaged with cosmetic or health care products and applications. For instance, the graphic and/or message display system can serve as a reminder for when a hair care or skin care application or treatment is completed (e.g., perms, colorants, facials, topical treatment, bleaching, etc.), or could be used as a reminder against over exposure in a spa environment, such as in hot-tubs or saunas. Also, the graphic and/or message display system can be used by hobbyists as a reminder for when etching solutions, paint remover, glues, and so forth have been applied or mixed for an appropriate length of time (e.g., epoxy, paint, etc.).

The graphic and/or message display system provides a noiseless, silent reminder device. The graphic and/or message display system can serve as a child-friendly reminder during, for example, sun exposure (e.g., when to apply or reapply sun screen, or when to get out of the sun), length of television watching, length of playtime or time-outs, or any other situation in which one can't or it may be inconvenient to refer to a clock.

A practical application of the graphic and/or message display system can be employed in the conditioning and training of children, in general, and for potty training in particular. For instance, the graphic and/or message display system may be incorporated as part of a training pant for conditioning a child to develop bladder control by providing a positive feedback at a particular time during the use of the product (e.g., 2-4 hours, or 3-6 hours). As such, the graphic and/or message display system can be both a child-friendly and child-appropriate positive reinforcement device.

Potty training a young child typically includes a wide variety of different aspects, including many training techniques and training aids that may be useful to parents and caregivers, hereinafter referred to simply as caregivers. One feature of potty or toilet training is having the young child change from wearing diapers to wearing training pants to help the child understand that he or she should now use the commode just like adults. An additional feature of the potty training process includes caregiver instruction and feedback as a positive encouragement and reinforcement to the child that he or she should now be using the toilet instead of diapers. Although the use of training pants and positive encouragement or feedback from caregivers has been helpful and is recommended for the training process, there still is room for improvement in providing more positive feedback mechanisms. Specifically, caregivers continue to search for alternative reward systems to guide their children successfully through the potty training process.

At the present, few, if any, products on the market can provide a positive feedback mechanism for children who are of potty training age, even though providing positive feedback is strongly encouraged by the majority of training programs (See B. Spock, M. D., and M. B. Rothenberg, M. D., *Dr. Spock's Baby and Child Care*, 6$^{th}$ Ed., pp. 457-475, ISBN: 0-671-75967-1, Pocket Books, 1992; or Wall Street Journal, "*Un-Pampered: Tots Face Strict Deadline on Toilet Training*," pp. A1, A6, Aug. 27, 2004.).

As a general consensus among child rearing experts, and as described in various parenting guides, positive reinforcement is preferred for training or conditioning a child to an activity. For example, when potty training, positive feedback can be a valuable training tool, which aides in the conditioning of self-control. It is envisioned that when applied to the outside of a personal care product, such as children's training pants, the graphic and/or message display system can provide the child a greater feeling of control and ownership in the child's potty training efforts, at an age where the child wishes to assert his or her independence. This, in turn, contributes to a positive feedback system of reward or affirmation for the child, which can motivate the child to try to maintain dryness for longer periods. It is envisioned that the graphic and/or message display system can be adapted to be a tool that can provide or instill a sense of empowerment or independence in a child by providing the child with the ability to supervise or control over his or her own behavior.

Young children have a well developed ability to recognize visual changes. Hence, the graphic and/or message display system can be employed as a training aid for children. The system takes advantage of the child's visual skill development to achieve a training goal with a visual representation of a positive feedback graphic or message. The child can be encouraged to maintain dryness so as to extend the wearing of the product for a given period of time, the length of which can increase as the training progresses and the child's self-control increases.

As a training aid for children during potty training, it is envisioned that the present graphic and/or message display system can be formed as part of a diaper, training pant, or other personal care product itself or as an add-on that can be purchased separately. The system would be activated once the caregiver has put the diaper on the child. Initially as potty training begins, the target or predetermined development time would be for about 2-3 hours. As the child's ability to exercise self-control improves, the caregiver can increase the duration with other indicators designed for longer development times (i.e. 4-5 hours, or 8 hours for overnight use).

According to an embodiment, a positive reinforcement graphic is situated on the indicator display area. Using a masking solvatochromic dye, the positive reinforcement graphic is covered or obscured by the dye. The solvent can enter into the solvatochromic dye and cause the hidden graphic to appear at the desired time.

The application of the solvent strip can be done by either a caregiver or a child when the product is placed on the child. The activation time can be designed to take from about 2-4 or 6 hours, based on the materials used and conditions set.

It is contemplated that the graphic and/or message display system in addition to being used for child or adult care incontinence articles can be adapted and incorporated into a variety of diverse products and articles for different applications. For examples, the graphic and/or message display system may be used to monitor the length of time the article has been worn or used. The device may be an indicator in a glove, surgical or medical gowns, drapes, bandages or dressings. According to health care guidelines, health care workers should change gloves at least every 2 hours. However, this may be seldom adhered to, leading to punctures and cross-contamination issues. This application is achieved by a simple graphic that fades within the requisite time frame to reveal a message alerting the user to change the gloves.

The present invention may be better understood by reference to the Examples below. However, it is to be understood that the invention is not limited thereto.

EXAMPLE 1

The use of chameleon type solvatochromic dyes to display hidden messages or graphics was demonstrated as follows. Reichardt's dye (available from Aldrich Chemical Company of Milwaukee WI). The Reichardt's dye was dissolved into acetonitrile (160 mg/10 ml) and the solution was applied to a plastic sheet (overhead transparency, Hewlett-Packard Company, Palo Alto Calif.) with a dropper to form a row of small colored circles each the size of a dime. The liquid was allowed to dry in a fume hood to give a solid color spot. A thin layer of office rubber cement (Ross Products, Inc., Columbus Ohio) was applied to the spots of dye with a brush and the color of the circles was observed with time. Over time, the color of the dye was discharged, resulting in a colorless transparent area after 2 hours. It is theorized that the dye slowly diffused into the glue and turned colorless due to the change in the polarity of the dye's environment.

EXAMPLE 2

Figure 4:
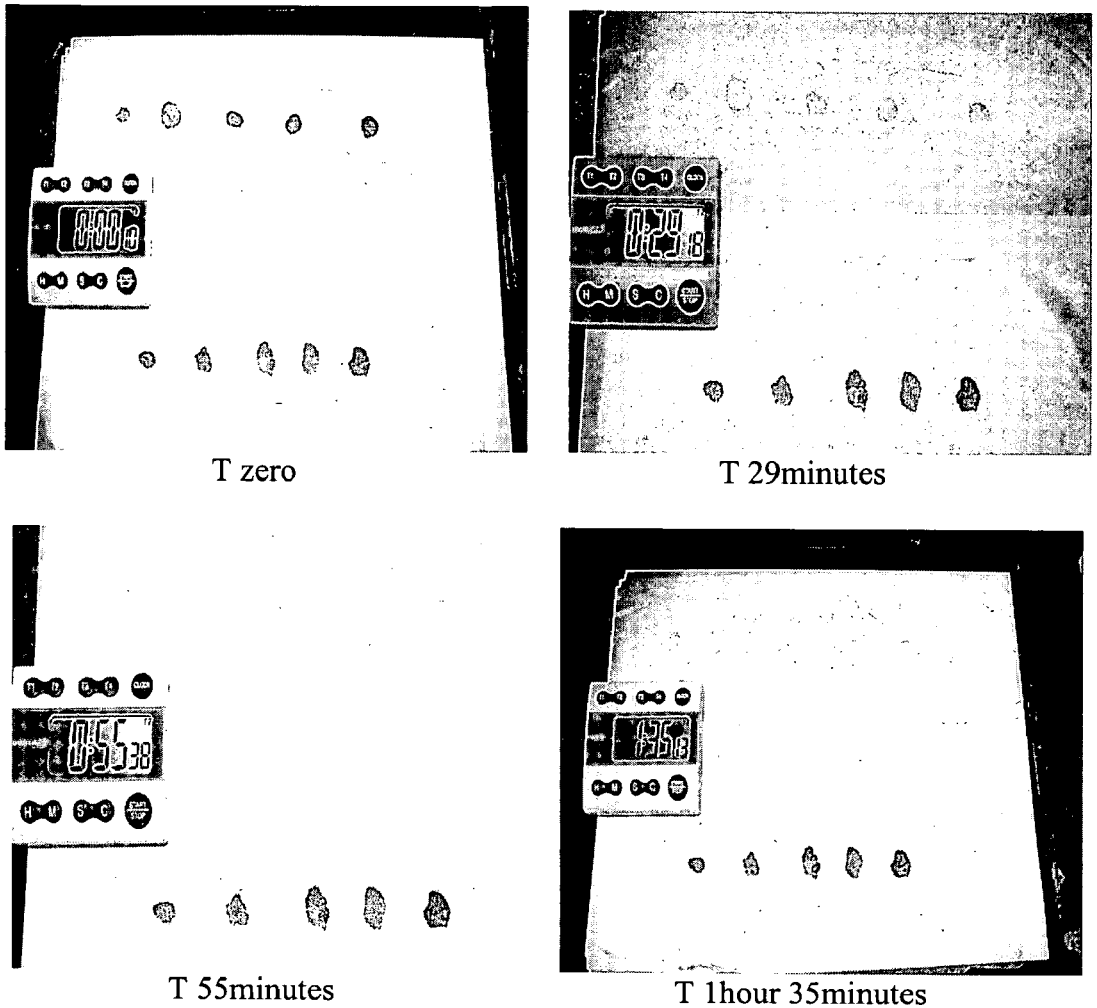
FIG. 4 depicts the effect of a solvent on a solvatochromic dye over time.

Example 1 was repeated with the difference that adhesive tape (Scotch magic tape, 3M, St. Paul Minn.) was applied to the spots of Reichardt's dye in lieu of rubber cement. As in Example 1, the color of the dye was discharged, resulting in a colorless transparent area after 2 hours. FIG. 4 depicts the discharge of the color by the adhesive on the tape over time at ambient temperature. The row of dots at the top of the sample in FIG. 4 is covered by adhesive tape while the bottom row has no tape and serves as a control. After 1 h 35 min the blue dye had completely turned colorless.

EXAMPLE 3

Figure 5:
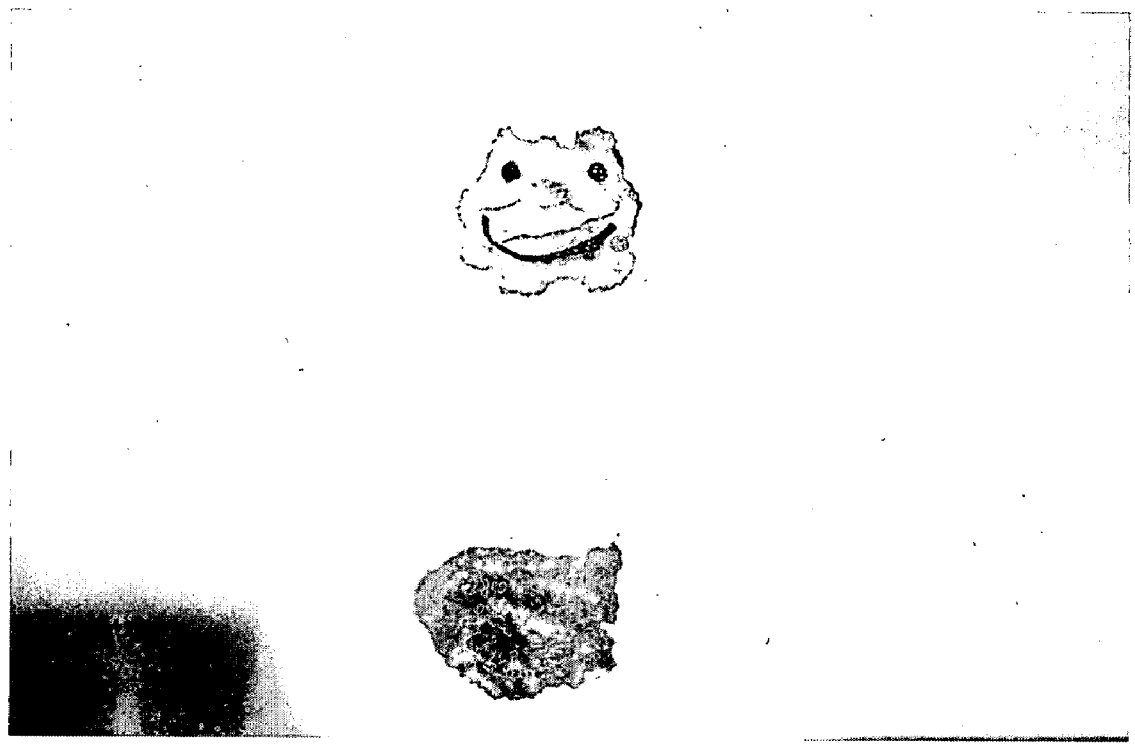
FIG. 5 depicts a hidden graphic revealed by activation of a solvatochromic dye by a solvent.

A SHARPIE® pen was used to generate two "hidden" ink graphics ("Happy Face" images) on a plastic sheet (GLAD cling films and overhead transparencies, Hewlett-Packard Company, Palo Alto Calif.). The hidden graphics were then covered with the Reichardt's dye solution from Example 1 to obscure the images. After the Reichardt's dye dried, one of the graphics was covered by a piece of packing tape. After 1 hour the Reichardt's dye color was discharged to reveal the underlying image. FIG. 5 shows both the obscured control graphic with no packing tape 10 and the revealed graphic 20 upon which the packing tape was placed. The time taken to reveal the image was found to be controlled by the thickness of the Reichardt's dye coating. Laboratory experiments demonstrated the image could be controlled to appear in the range from about 1 to about 5 hours. SCOTCH brand adhesive tapes were also demonstrated to be effective for revealing the hidden graphic.

EXAMPLE 4

Figure 6:
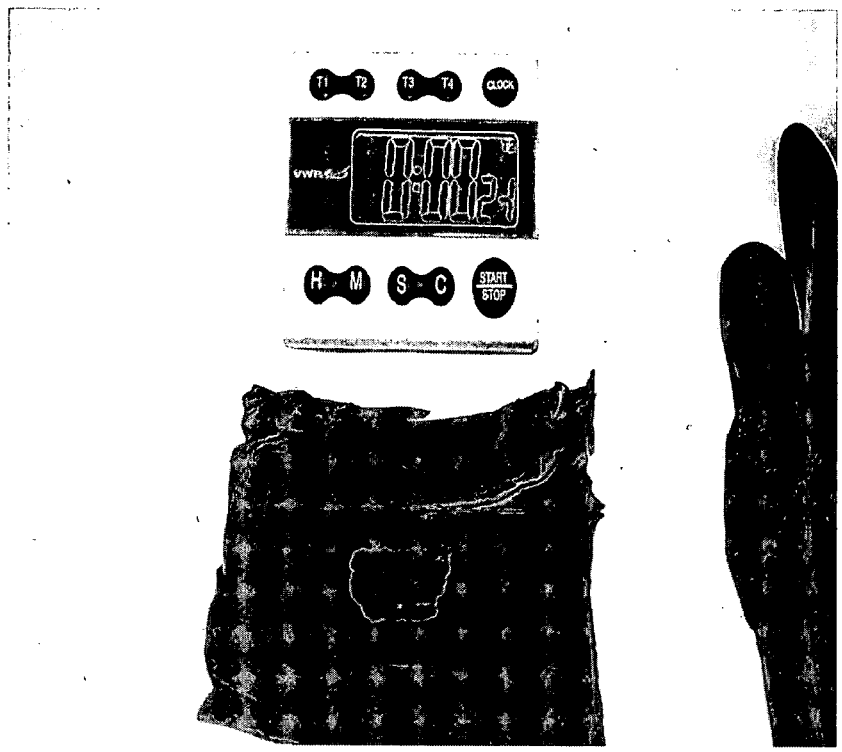
FIG. 6 is a set of photos depicting the appearance of a hidden graphic revealed by activation of a solvatochromic dye by a solvent.
Figure 6:
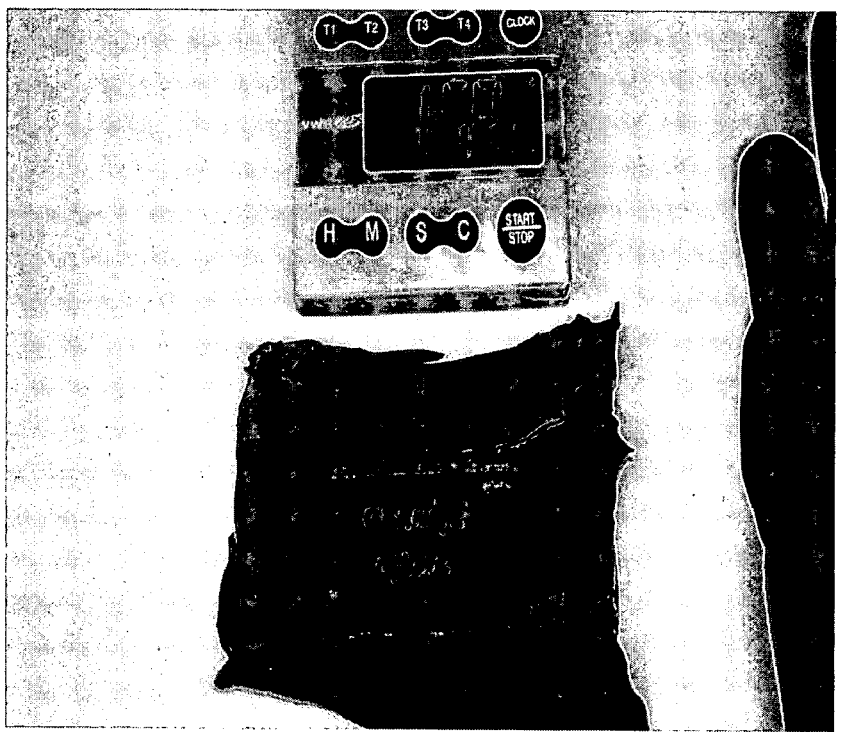

A simple visual indicator message for surgical gloves to inform or alert the user that it is time to change their gloves was demonstrated. A standard purple nitrile glove (available from Kimberly-Clark Corporation, Dallas, Tex.) was used. On the area of the glove on the back of the hand was written "Change Glove" using a standard SHARPIE® pen. Next, the solution of the Reichardt's dye from Example 1 was brushed onto the pen ink area to coat and cover the message. A small piece of standard SCOTCH® clear tape was placed onto the masked area and pressed to make contact. As the photographs in FIG. 6 illustrate, the masking dye decolorized after 2 hours to reveal the "Change Glove" message.

EXAMPLE 5

Additional pyridinium N-phenoxide betaines, of which Reichardt's dye is a member, were tested with adhesive tape to determine if they also underwent a color change similar to Reichardt's dye. Samples of 2,6-dichloro-4-(2,4,6-triphenyl-N-pyridinio)-phenolate (Betaine 1) and 1-(4-hydroxyphenol)-2,4,6-triphenylpyridinium hydroxide (Betaine 2) were used in the study.

Betaine 1 was prepared by dissolving 2,4,6-triphenyl-N-pyrylium hydrogen sulfate (0.63 g, 1.6 mmole) and 4-amino-2,6-dichlorophenol (0.33 g, 1.87 mmole) in hot 100% ethanol (50 ml). After the addition of anhydrous sodium acetate (0.29 g, 3.5 mmole), the mixture was heated to reflux for 3 hours.

Then, a 5% aqueous solution of sodium hydroxide (50 ml) was added to the hot solution and the ethanol was removed under vacuum to yield deep purple crystals, which were first washed with 1% sodium hydroxide solution until the washing liquid became pale yellow. Finally, they were washed well with distilled water. The resulting powder was then dried in a vacuum desiccator for 24 hours to yield a red powder (0.46 g, 59%).

Betaine 2 was prepared by placing 4-aminophenol (2.8 g, 10.7 mmole) and 2,4,6-triphenylpyrylium hydrogen sulfate (4.1 g, 10.1 mmole) in ethanol (50 ml) and heating to dissolve. After addition of sodium acetate (4.0 g) the mixture was refluxed for 3 hours. Then, 5% wt/wt sodium hydroxide solution (25 ml) was added to the hot solution and the major part of the ethanol was removed under vacuum on a rotovap to leave blue crystals. The blue crystals were then filtered and washed with water until the filtrate was colorless. The powder was then dried in a vacuum desiccator to yield 3.1 g (51%). The structure was confirmed by NMR (acetonitrile-D3).

Betaine 1 and Betaine 2 dye samples were then prepared as acetonitrile solutions (160 mg/10 ml) and drops of the solutions were placed onto a transparency film and allowed to dry. The spots were then covered with clear adhesive tape and observed. After 2 hours the betaines did not turn colorless, rather they changed color. The Betaine 1 changed from a dark purple to a bright red and the Betaine 2 changed from a brown to bright yellow. Therefore, the Betaine 1 would be useful for obscuring a dark purple hidden graphic because the original color of the Betaine 1 would match the color of the hidden graphic, thus obscuring the hidden graphic. When the Betaine 1 changes color, the underlying purple graphic will appear. Likewise, the Betaine 2 would be useful for obscuring a brown graphic. The original brown color of the Betaine 2 would obscure the brown color of the hidden graphic. When the Betaine 2 changes color, the underlying brown graphic will appear.

EXAMPLE 6

A blue solvatochromatic dye could be mixed with a color-stable (non-solvatochromatic) yellow dye to create a green dye mixture. The green dye mixture could be used to create a "change glove" message on a similarly colored green glove. Because the green dye and the green glove would be similar in color, the message would not initially be readily visible on the glove. A user of the glove could apply a piece of standard transparent tape to the glove over the graphic. The adhesive on the tape would react with the solvatochromatic dye to render it transparent or colorless, thus changing the color of the graphic to the color of the color-stable dye, i.e., yellow. The yellow graphic would then be evident to the wearer against the background of the green glove. Other color combinations are possible. For example, a red solvatochromatic dye could be mixed with a green color-stable dye to create a brown mixture. Reaction with a solvent or adhesive gel could transform the mixture to a green color.

While the specification has been described in detail with respect to specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto. Further, it is recognized that many embodiments may be conceived that do not achieve all of the advantages of some embodiments, yet the absence of a particular advantage shall not be construed to necessarily mean that such an embodiment is outside the scope of the present invention. In addition, it should be noted that any given range presented herein is intended to include any and all lesser included ranges. For example, a range of from 45-90 would also include 50-90; 45-80; 46-89 and the like. Thus, the range of 95% to 99.999% also includes, for example, the ranges of 96% to 99.1%, 96.3% to 99.7%, and 99.91% to 99.999%, etc.

We claim:

1. A visual indicator system comprising an indicator panel having a graphic region with a hidden message graphic and a masking graphic comprising a solvatochromic dye, and a solvent applicator comprising a substantially transparent sheet-like substrate having first and second surfaces, and a solvent disposed on the first surface of the substrate between the substrate and the masking graphic, the size of the sheet-like substrate corresponding to the size of the masking graphic.

2. The visual indicator system according to claim 1, wherein the visual indicator system is a glove.

3. The visual indicator system according to claim 1, wherein the indicator panel is either a substantially two-dimensional visual display or is part of a three-dimensional shaped surface or article.

4. The visual indicator system according to claim 1, wherein the solvent is a fluid.

5. The visual indicator system according to claim 4, wherein the fluid is a liquid, a gel, or a semi-solid.

6. The visual indicator system according to claim 1, wherein the solvatochromic dye is a zwitterionic chromogen.

7. The visual indicator system according to claim 6, wherein the zwitterionic chromogen is Reichardt's dye.

8. The visual indicator system according to claim 1, wherein the solvatochromic dye is a merocyanine.

9. The visual indicator system according to claim 1, wherein the solvatochromic dye comprises a compound having the formula

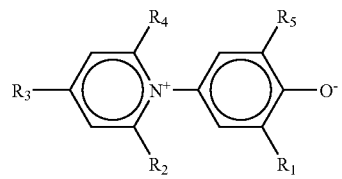

wherein $R_1$, $R_2$, $R_3$, $R_4$, and $R_5$ are selected from the group consisting of phenyl, benzyl, pyridinyl, aryl, heteroaryl, alkyl ($C_1$-$C_{12}$), cycloalkyl, heterocyclo, halide, chlorine, fluorine, hydrogen, amido, amine, and thiol groups.

10. The visual indicator system according to claim 1, wherein the masking graphic is colored.

11. The visual indicator system according to claim 1, wherein the message graphic is colored.

12. The visual indicator system according to claim 1, wherein the masking graphic and the message graphic are differently colored.

13. The visual indicator system according to claim 1, wherein the indicator panel is activated when the solvent on the solvent applicator is placed against the indicator panel, establishing controlled communication between the solvent and the masking graphic.

14. The visual indicator system according to claim 1, wherein the indicator panel is either a stand alone article in the personal care article or can be incorporated as part of a component of the personal care article.

* * * * *